United States Patent [19]
Friedman

[11] Patent Number: 5,319,122
[45] Date of Patent: Jun. 7, 1994

[54] PROCESS FOR THE PREPARATION OF BENZYLFORMIMIDATE

[75] Inventor: Joel J. Friedman, East Brunswick, N.J.

[73] Assignee: Merck & Co., Inc., Rahway, N.J.

[21] Appl. No.: 975,306

[22] Filed: Nov. 12, 1992

[51] Int. Cl.$^5$ .................. C07C 249/02; C07C 249/04
[52] U.S. Cl. .......................................... 558/6; 560/12; 560/23; 560/20; 560/35; 562/429; 562/432; 562/434; 562/437; 562/438; 562/440; 564/256
[58] Field of Search .............. 564/256; 560/12, 20, 560/23, 35; 562/429, 432, 434, 439, 438, 440; 558/6

[56] References Cited

U.S. PATENT DOCUMENTS

| | | | |
|---|---|---|---|
| 4,039,554 | 8/1977 | Koenig et al. | 562/80 |
| 4,194,047 | 3/1980 | Christensen et al. | 562/80 |
| 4,374,772 | 2/1983 | Hazen et al. | 562/80 |
| 4,820,817 | 4/1989 | Christensen et al. | 562/80 |
| 4,845,261 | 7/1989 | Fuentes | 562/80 |
| 4,894,450 | 1/1990 | Grabowski et al. | 562/80 |
| 5,021,566 | 6/1991 | Christensen et al. | 562/80 |
| 5,147,868 | 9/1992 | Graham et al. | 562/80 |

FOREIGN PATENT DOCUMENTS

WO92/06978 4/1992 PCT Int'l Appl. .

*Primary Examiner*—Johann Richter
*Attorney, Agent, or Firm*—Hesna J. Pfeiffer; Mark R. Daniel

[57] ABSTRACT

This invention relates to a novel process for preparing benzylformimidates which are useful in the production of certain carbapenem antibiotics. The process of this invention provides a means of producing a high-yield, high-purity product.

2 Claims, No Drawings

PROCESS FOR THE PREPARATION OF BENZYLFORMIMIDATE

BACKGROUND OF THE INVENTION

The present invention relates to a novel process for preparing benzylformimidate utilizing tetrahydrofuran as the reaction solvent. In particular, this invention relates to a process for preparing benzylformimidate hydrochloride, a compound which is required in the manufacture of certain carbapenem antibiotics, utilizing tetrahydrofuran as the reaction solvent.

Various processes for the manufacture benzylformimidate have been disclosed in the art. U.S. Pat. No. 4,194,047 discloses a process for preparing ethyl N-Benzylformimidate utilizing methylene chloride in the reaction process.

U.S. Pat. No. 4,374,772 discloses a process for preparing N-formimidoyl thienamycin utilizing benzylformimidate hydrochloride in the reaction process. Unlike the process of the present invention, U.S. Pat. No. 4,374,772 discloses using ethyl ether as the reaction solvent in the preparation of the product. Ethyl ether is a very hazardous compound.

It has been surprisingly discovered that the use of tetrahydrofuran as a reaction solvent in the preparation of benzylformimidate will produce a high-yield, high-purity product.

It is, therefore, an object of the present invention to provide a novel process for the preparation of benzylformimidate. It is also an object of this invention to provide a process for the preparation of benzylformimidate hydrochloride utilizing tetrahydrofuran as the reaction solvent in order to prepare a high-yield, high-purity product.

SUMMARY OF THE INVENTION

The present invention provides a process for the preparation of a compound having the formula:

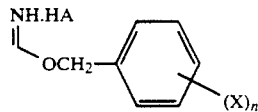

wherein:
X is nitro, halogen, $C_1$-$C_6$alkyl, phenyl, $C_7$-$C_{12}$phenylalkyl, or —COOR, wherein R is hydrogen or $C_1$-$C_6$alkyl;
A is chlorine, bromine, hydrogen sulfate, $C_1$-$C_6$alkyl, $C_1$-$C_6$aralkyl or aryl sulfonate; or
n is 1, 2, or 3;
comprising reacting the compound of formula I with a tetrahydrofuran reaction solvent in order to prepare a high-yield, high-purity product.

DETAILED DESCRIPTION OF THE INVENTION

The present invention provides a novel process for the preparation of a compound having the formula:

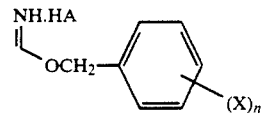

wherein:
X is nitro, halogen, $C_1$-$C_6$alkyl, phenyl, $C_7$-$C_{12}$phenylalkyl, or —COOR, wherein R is hydrogen or $C_1$-$C_6$alkyl;
A is chlorine, bromine, hydrogen sulfate, $C_1$-$C_6$alkyl, $C_1$-$C_6$aralkyl or aryl sulfonate; or
n is 1, 2 or 3;
comprising reacting tetrahydrofuran with benzylic alcohol, formamide and an aryl chloride to give the desired formimidates as stable crystalline salts.

The preferred embodiment of this invention involves a process for preparing benzylformimidate hydrochloride of the formula:

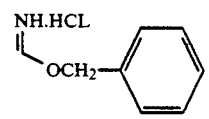

comprising the steps of:
a) mixing tetrahydrofuran with benzyl alcohol and formamide;
b) cooling the reaction mixture to about +5° C. to about −5° C.;
c) adding benzoyl chloride to the reaction mixture at rate to maintain a temperature range of about +5° C. to about −5° C. to about −5° C;
d) aging the reaction mixture for about two hours at a temperature of about +5° C. to about −5° C.;
e) adding acetic anhydride to the reaction mixture and continuing aging for about 30 minutes at about +5° C. to about −5° C.;
f) filtering the product under a blanket of nitrogen and displacement wash; and
g) vacuum drying the product cake at room temperature for about 3 to about 4 hours.

The term "halogen" includes chlorine, bromine, flourine or iodine.

The term "$C_1$-$C_6$ alkyl" includes straight and branched chain alkyl groups having 1 to 6 carbons. The term $C_1$-$C_6$ alkyl includes methyl, ethyl, propyl, isopropyl, butyl, sec-butyl, t-butyl, n-pentyl, and the like.

The following scheme illustrates a reaction sequence in which the process of the present invention is employed.

REACTION SCHEME

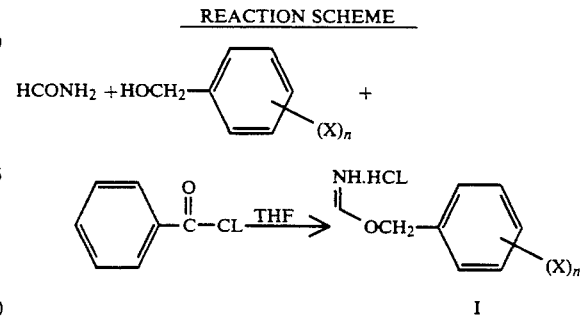

The compound of formula I is prepared by the reaction of formamide, benzoyl chloride and the desired benzylic alcohol in the presence of tetrahydrofuran to give the desired formimidates as stable crystalline salts. In addition to benzoyl chloride the following may be used, alkyl acyl chlorides, aryl acyl chlorides, acyl bromides, or mixed alkyl, aryl acyl chlorides.

The substituted and unsubstituted benzylformimidates of formula I:

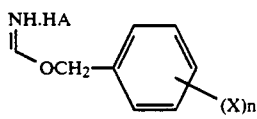

may be utilized in the process for preparing N-formimidoyl thienamycin (II)

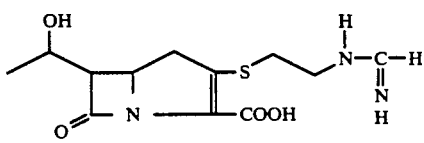

from thienamycin (III)

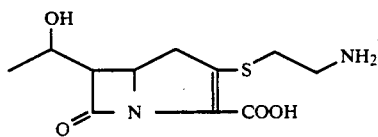

The process for preparing N-formimidoyl thienamycin (II) from the benzylformimidates of formula I is represented by the reaction below:

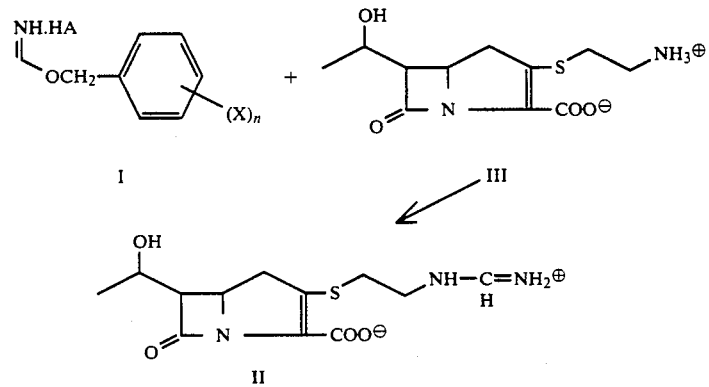

wherein all symbols have previously been defined. Typically, the ratio of reagent I to thienamycin is from about 1.5:1 to about 10:1. The most preferred reaction ratio being about 6 to 1.

The novel process of this invention exhibits many advantages when compared to the prior art process in which methylene chloride was the reaction solvent. In the present invention the yield of benzylformimidate hydrochloride was significantly increased from about 69% to about 92–93%. Purity of the product improved from about 94% to about 98% to 100% purity. The product capacity of the product improved 100% due to the 50% reduction in solvent. The time cycle was reduced to a broader temperature operating range. The wet and dry stability of the product has been found to be excellent at about 20° to about 25° C., while it was previously unstable at temperature greater than 0° C. The process of this invention was further able to reduce the use of acetic anhydride by about 75% improving waste minimization.

EXAMPLES

Examples provided are intended to assist in a further understanding of the invention. Particular materials employed, species and conditions are intended to be further illustrated of the invention and not limitative of the reasonable scope thereof.

EXAMPLE 1 preparation of benzylformimidate hydrochloride

A 500 ml 4-neck R.B. flask fitted with an addition funnel, overhead mechanical stirrer, thermometer, reflux condenser and nitrogen inlet (+pressure) is charged with a mixture of tetrahydrofuran (THF) (140 ml), benzyl alcohol (42 ml) (mw 108, d 1.041, 43.6 gm, 0.404 mole), and formamide (16.06 ml) mw 45, d 1.133, 18.2 gm, 0.404 mole).

The reaction mixture is cooled to about 0° C. (about +5° C. to about −5° C. desired range) and benzoyl chloride (48.2 ml) (mw 140, d 1.207, 58.2 gm, 0.416 mole) is slowly added dropwise using the addition funnel at a rate to maintain the desired temperature range (about 5° C. to about −5° C.) for about 1.5 hours. Upon completion of the addition of benzoyl chloride to the reaction mixture, the reaction mixture is allowed to age for about 2 hours at about 0° C.

Upon completion of the aging, acetic anhydride (22.5 ml) (mw 102, d 1.08, 24.3 gm, 0.238 mole) is added dropwise using the addition funnel at about 0° C. for about 30 minutes. The reaction product is subsequently filtered under a blanket of nitrogen and displacement wash cake (3×50 ml) (centrifuge wash may be lower volume) with cold virgin THF. The reaction product is vacuum dried at room temperature for about 3 to 4 hours to give about 64 to about 66 gm (94% to 96% yield) of benzylformimidate hydrochloride as a white solid.

What is claimed is:

1. A process for the preparation of a compound having the formula:

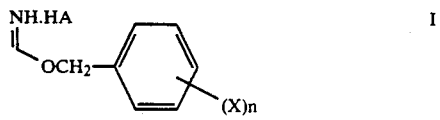

wherein:

X is nitro, halogen, $C_1$–$C_6$alkyl, phenyl, $C_7$–$C_{12}$ phenylalkyl, or —COOR, wherein R is hydrogen or $C_1$–$C_6$alkyl;

A is chlorine, bromine, hydrogen sulfate, $C_1$–$C_6$alkyl, $C_1$–$C_6$aralkyl or aryl sulfonate; or n is 1, 2 or 3;

comprising reacting tetrahydrofuran with benzylic alcohol, formamide and an aroyl chloride to give the desired formimidates as stable crystalline salts.

2. A process for the preparation of a compound having the formula:

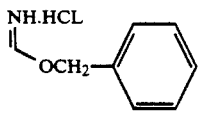

comprising the steps of:

a) mixing tetrahydrofuran with benzyl alcohol and formamide;
b) cooling the reaction mixture to about +5° C. to about −5° C.;
c) adding benzoyl chloride to the reaction mixture at rate to maintain a temperature range of about +5° C. to about −5° C.;
d) aging the reaction mixture for about two hours at a temperature of about +5° C. to about −5° C.;
e) adding acetic anhydride to the reaction mixture and continuing aging for about 30 minutes at about +5° C. to about −5° C.;
f) filtering the product under a blanket of nitrogen and displacement wash; and
g) vacuum drying the product cake at room temperature for about 3 to about 4 hours.

* * * * *